US007123363B2

United States Patent
Puttappa et al.

(10) Patent No.: US 7,123,363 B2
(45) Date of Patent: Oct. 17, 2006

(54) SPECKLE PATTERN ANALYSIS METHOD AND SYSTEM

(75) Inventors: Jayanth Puttappa, Terre Haute, IN (US); Charles Joenathan, Terre Haute, IN (US); Brij M Khorana, Terre Haute, IN (US)

(73) Assignee: Rose-Hulman Institute of Technology, Terre Haute, IN (US)

( * ) Notice: Subject to any disclaimer, the term of this patent is extended or adjusted under 35 U.S.C. 154(b) by 248 days.

(21) Appl. No.: 10/751,159

(22) Filed: Jan. 2, 2004

(65) Prior Publication Data

US 2004/0152989 A1     Aug. 5, 2004

Related U.S. Application Data

(60) Provisional application No. 60/437,961, filed on Jan. 3, 2003.

(51) Int. Cl.
*G01B 9/02* (2006.01)
*G01B 11/02* (2006.01)

(52) U.S. Cl. ............................ 356/450; 356/511
(58) Field of Classification Search ........... 356/450, 356/511, 512
See application file for complete search history.

(56) References Cited

U.S. PATENT DOCUMENTS

| | | | |
|---|---|---|---|
| 4,824,250 A * | 4/1989 | Newman | 356/502 |
| 5,090,799 A * | 2/1992 | Makino et al. | 351/221 |
| 5,551,422 A | 9/1996 | Simonsen et al. | |
| 5,585,921 A * | 12/1996 | Pepper et al. | 356/487 |
| 5,598,841 A | 2/1997 | Taniji et al. | |
| 5,617,852 A | 4/1997 | MacGregor | |
| 5,628,310 A | 5/1997 | Rao et al. | |
| 5,710,630 A | 1/1998 | Essenpreis et al. | |
| 5,748,311 A | 5/1998 | Hamann et al. | |
| 5,784,162 A | 7/1998 | Cabib et al. | |
| 5,841,030 A * | 11/1998 | Honsberg et al. | 73/579 |
| 5,876,342 A * | 3/1999 | Chen et al. | 600/443 |
| 5,897,494 A * | 4/1999 | Flock et al. | 600/407 |

(Continued)

OTHER PUBLICATIONS

Brij M. Khorana, "Lasers in diagnostic dentistry," Lasers in Medicine and Dentistry: Diagnostics and Treatment, Nov. 4-5, 1996, vol. 2887, SPIE, Beijing, China.

(Continued)

*Primary Examiner*—Hwa (Andrew) Lee
*Assistant Examiner*—Patrick Connolly
(74) *Attorney, Agent, or Firm*—Baker & Daniels LLP

(57) ABSTRACT

The present invention involves a system for measuring biospeckle of a specimen. The system includes a source of coherent light, such as a laser, capable of being aimed at a specimen; a camera capable of obtaining images of the specimen; and a processor coupled to the camera. The processor has software capable of performing bio-activity calculations on the plurality of images. The bio-activity calculations may include a Fourier Transform Analysis, Power Spectral Density, Fractal Dimensional Calculation, and/or Wavelet Transform Analysis. The camera is capable of obtaining at least one hundred images per second. The software is capable of conversion of 8-bit bmp images to intensity values, calculating a PSD on said plurality of images.

30 Claims, 4 Drawing Sheets

U.S. PATENT DOCUMENTS

| | | | |
|---|---|---|---|
| 5,991,697 | A | 11/1999 | Nelson et al. |
| 6,317,506 | B1 | 11/2001 | Helbig et al. |
| 6,352,517 | B1 | 3/2002 | Flock et al. |
| 6,700,666 | B1 * | 3/2004 | Blouin et al. .............. 356/502 |
| 6,809,991 | B1 * | 10/2004 | Pepper et al. .............. 367/149 |
| 6,944,494 | B1 * | 9/2005 | Forrester et al. ........... 600/478 |
| 6,970,251 | B1 * | 11/2005 | Vikhagen .................. 356/496 |
| 2002/0183601 | A1 | 12/2002 | Tearney et al. |
| 2003/0120156 | A1 | 6/2003 | Forrester et al. |

OTHER PUBLICATIONS

Zijie Xu, Charles Joenathan, Brij M. Khorana, Temporal & Spatial Properties of the Time-Varying Speckles of Botanical Specimens, Optical Engineering, May 1995, vol. 34 No. 5.

Jayanth Puttappa, Charles Joenathan, & Brij M. Khorana, "Time-varying Speckle Patterns in the Study of Aging of Bio-specimens" (B026), BIOS-03 Conference, Jan. 25-30, 2003.

* cited by examiner

SPECKLE PATTERN ANALYSIS METHOD AND SYSTEM

This applications claims the benefit of U.S. Provisional Application No. 60/437,961 filed on Jan. 3, 2003.

BACKGROUND OF THE INVENTION

1. Field of the Invention

The field of the invention is that of measurement of vibrations. In particular, the field is that of speckle analysis of biological and microscopic systems.

2. Description of the Related Art

The phenomenon of dynamic speckle is observed when an object under investigation is illuminated with coherent laser radiation. Laser-induced speckle patterns have found applications in studying bio-specimens non-invasively. Living cells or tissues of bio-specimens create complex and randomly varying 'bio-speckles' that are characteristic signatures of the specimen.

Lasers have found their way in biomedical applications because of the properties of power, high coherence and low beam divergence. When a low power laser illuminates a surface, light is scattered in all directions. These scattered light rays in turn interfere with each other causing a localized microscopic interference pattern called speckle. The term bio-speckle refers to speckle pattern detected on a biological specimen. The speckle pattern has both temporal and spatial characteristics. In the time domain the speckle pattern is directly related to changes taking place that effect the scattering of light. An inanimate object is time-invariant and thus has no temporal component. An animate object, however, will yield a time-varying speckle pattern as the geometry and surface alter. The change may come from the object moving as a whole, or as the compositional elements within move. Regardless of where the dynamic behavior occurs, there is an observed phase shift. In the case of compositional elements moving within a living structure or tissue, a continuously changing pattern will be observed. This 'boiling' speckle is referred to as the biospeckle and has been observable in objects such as fruit, vegetables, blood flow, and egg embryos.

This speckle pattern is directly related to the rate at which the compositional elements within the structure move i.e., the bioactivity. Most macroscopic living organisms are composed of a thin semi-permanent membrane (skin) and compositional elements moving within, whether these be blood cells, plasma, chromoplasts in plants, or other smaller parts of the cell. The laser light penetrates past the surface (dermal) layers and into the tissue beneath. Cells are composed of hundreds of smaller components moving within the cytoplasm. It should be a reasonable conjecture that all moving elements do not have the same speed. If the elements are large enough to backwards scatter the light, then each part of the cell that moves should have an observable velocity relationship.

Laser-induced speckle patterns have found applications in studying microscopic vibrations of inanimate systems non-invasively. Several such systems vibrate with one or more frequency of oscillations. These vibrations have very small positional displacements on the order of a few to several nanometers. These systems create temporal varying speckles that are characteristic signatures of their particular systems. In the case of compositional elements moving within a vibrating structure, a continuously changing pattern will be observed. This temporally varying speckle is characteristic to vibrations which have been observable in inanimate objects such as a vibrating surface on a micro-switch, micro-actuator, or micro-motor used in nanotechnology type devices.

However, previous attempts at analyzing speckle patterns have been unsuccessful in providing predictable results. What is needed is a more accurate analysis of vibrations to provide more meaningful evaluations of living structures, tissues, or nanotechnology.

SUMMARY OF THE INVENTION

The present invention, in one form thereof, involves a system and method for measuring speckle caused by microscopic vibrations of a specimen or system. A source of coherent light, such as a laser, is aimed at a specimen or system. The coherent light beam may penetrate into a suitable specimen and scatter from the surface as well as from within the material of the specimen. Additional information may be obtained by vibrating the specimen and observing characteristic speckle from the vibrating specimen. A camera obtains a plurality of images of the specimen or system. A processor coupled to the camera includes software which performs Fourier Transform (FFT) calculations on the images. The camera is capable of obtaining at least one hundred images per second and has memory size capable of storing greater than 300 images. The software is capable of calculating a Power Spectral Density (PSD) analysis on the images. In addition to FFT and PSD analysis, the software is also capable of performing Fractal Dimension Calculations (FDC) and Wavelet Transform Analysis (WTA) to further enhance the analysis of the present invention.

In one exemplary embodiment, a He—Ne laser (~10 mW) is utilized to illuminate a specimen or system under examination, for example plant tissues such as a leaf, flower or fruit or a micro-switch or a nanotechnology system. A high-speed camera that captures up to 32,000 frames per second collects the laser radiation scattered from the specimen or system. Each pixel in the camera records the time-varying intensity of the speckle. These intensity values are Fourier transformed and/or used to calculate Fractal Dimensions and/or Wavelet Transform analysis to obtain the characteristic "oscillation frequencies" of the specimen or system. We first demonstrate the apparatus for measuring the vibration frequencies of a speaker. The speaker is subjected to several frequencies from ~0.001 hertz to ~1000 hertz, and it is also possible to use a Piezoelectric transducer (PZT) for a similar detection. The speaker or PZT is also subjected to modulated frequencies consisting of low and high frequencies. These frequencies may be accurately detected by our apparatus. We then may extend the measurements to observe 'oscillation frequencies' of the specimen or system. Thus, the apparatus may determine the aging process involved in living tissues. Further, this suggests a correlation between the oscillation frequency and glucose levels in the human blood stream, showing a more general use of the inventive system and method. Also, the apparatus may be used to determine the operational state of a nanotechnology device non-invasively by analyzing the vibration characteristics of the system.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
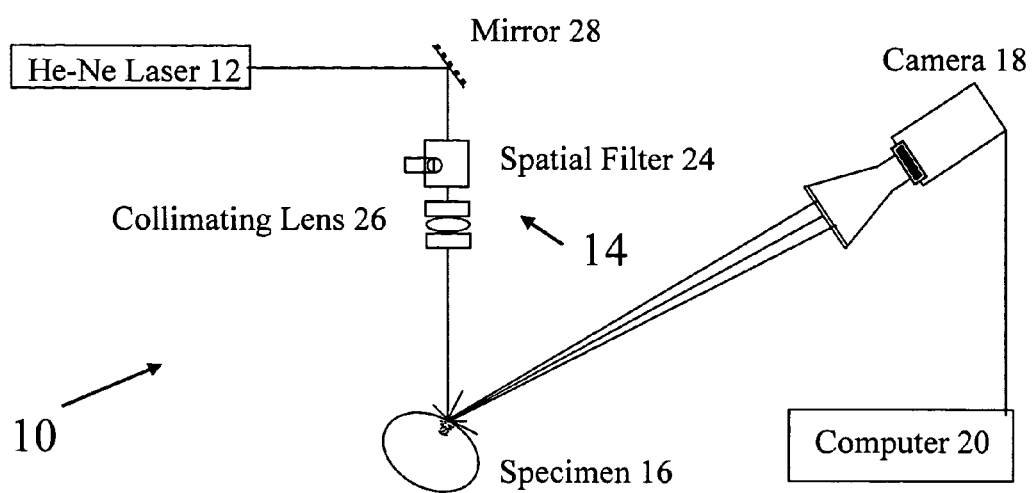
FIG. 1 is a schematic view of the system of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DESCRIPTION OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

The acronym L.A.S.E.R. ("laser") stands for Light Amplification by Stimulated Emission of Radiation. A laser is a device that produces and emits a coherent, concentrated and highly directional beam of light. Lasers are typically monochromatic in that they typically consist of one wavelength, and lasers work using light in the ultraviolet, infrared, and visible light spectrums. Continuous beam lasers emit a continuous beam of light while pulsed beam lasers emit light in single or multiple pulses. Such a coherent beam of light is capable of penetrating into a non-opaque specimen and some of the light will scatter out of the specimen to provide information about the activity within the specimen. The speckle formed from the surface provides information about the surface characteristics while the speckle formed within the specimen provides information about the interior characteristics.

The relevant statistical property used to describe the time-varying aspect of the speckle pattern is the power spectral density (PSD) of the spectral intensity. The PSD is a second order statistic that gives information about the velocity distribution of elements within the specimen and/or system. The important information that needs to be gathered is how the pattern at each individual position, pixel, changes with time. Stationary scatterers do effect the intensity reading but if enough samples are taken this can be neglected. After image frames are captured and converted to intensity readings, a pixel by pixel Fourier transform is executed. The result is the temporal PSD, which gives the frequency distributions with respect to time. To further analyze the readings, the values are averaged or normalized to obtain a single PSD spectrum. Either of two expressions for normalization may be used:

$$<PSD> = \frac{\sum_{n=0}^{N} I_{ij}}{\sum_{n=0}^{N} I_{ijMAX}} \text{ and } <PSD> = \frac{\sum_{n=0}^{N} \frac{I_{ij}}{I_{ijMAX}}}{N}$$

Where $I_{ij}$ is the intensity value of the $ij^{th}$ pixel, $I_{ijMAX}$ is the maximum value of the intensity for the $ij^{th}$ pixel and N is the total number of frames.

The relationship of frequency of vibration $\nu$ to frame rate $\alpha$, number of frames N, and the exposure Time $T_E$ should also be considered. In general, if we know at what frequency the surface under study is vibrating we can select the other above mentioned parameters. In accordance with the Nyquist theory two complete waveforms must be captured with at least two points within each waveform to generate the correct Fourier transform. For example:

If $\alpha$=500 frames/sec,

N=2000 frames in a waveform, $\nu$=0.5 Hz;

then the total lapsed time for the waveform is 2000 frames÷500 frames/sec. This is equal to T=4 sec.

Since $\nu$=0.5 Hz, time period t=1/$\nu$=2 sec/cycles. Thus number of cycles in a waveform=4 sec÷2 sec/cycle=2 cycles. In one exemplary embodiment, a minimum of 10 waveforms were captured with a minimum of 10 points each. The larger the number of images captured, the higher the frequency values may be detected by the system of the present invention. That is, the frequency responsivity (upper limit measurement) of the system increases as the number of images captured.

A relevant exposure time was one hundredth of the time it took for one oscillation. The exposure time was selected as $T_E$<<1/$\alpha$. The minimum value expected is 1/$\alpha$=3×$T_E$. From the exemplary embodiment in the following paragraph, the value of 1/$\alpha$=1/500=2 msec. That is, exposure time $T_E$=0.677 msec. Thus, the exposure time is around $\frac{1}{3}^{rd}$ the value of 1/$\alpha$. Standard image processing software may be used to convert images from any specific format captured by the camera to intensity values. Usually, this is conversion of 8 bit .bmp files to intensity values. Alternatively, Cin or Jpeg are the other formats that may be converted to 8 bit or 24 bit or higher intensity values. In the exemplary embodiment, programs using Labview-VI were written for this purpose of conversion of 8 bit bmp to intensity values. The same software may also be programmed for PSD calculation and normalization. Labview is a trademark of and produced by National Instruments Corporation of Austin, Tex.

FIG. 1 shows a diagram of system 10 of the present invention. laser 12 emits a coherent laser light which on passing through one or more optical element(s) 14 is expanded and cleaned of spatial frequencies, to illuminate specimen 16 (in this disclosure, specimen may refer to a biological specimen or a inanimate system). Scattered light from optical element(s) 14 is captured by camera 18. In the exemplary embodiment, optical elements 14 include mirror 28, spatial filter 24 and collimating lens 26. Images obtained by camera 18 are downloaded on computer 20 for further post-processing. In the disclosed embodiment, a low power He—Ne laser 12 of approximately ten milli-watts (~10 mW) is expanded, spatially filtered and collimated to a beam diameter of ~10 mm by mirror 28, spatial filter 24, and collimating lens 26. The spatial filtering cleans the laser beam thereby eliminating unwanted interference due to scattering from optical element(s) 14, which may include surfaces such as mirrors or lenses. The expansion and collimation of the beam is to have a larger area of specimen 16 (which in the exemplary embodiments may be a speaker or banana, or a MEMS or nanotechnology device) illuminated. The expanded and collimated beam illuminates specimen 16 as shown in FIG. 1, which includes light beams that have penetrated into the interior of specimen 16, for example by several millimeters, so that speckle from interior parts of specimen 16 may be processed. Camera 18, which in the disclosed embodiment is a high speed camera that may capture up to 32,000 frames per second, collects the laser radiation scattered from specimen 16, which may be observed by a speaker. Camera 18 records images sequentially at a high speed that can be processed by the user. These images may then be downloaded on to the hard-drive (not shown) of computer 20. These images may be stored as 'cin' files and may be converted into 'bmp' files. A commercially available software called Labview-VI may convert the bmp files to intensity files. These intensity files give the intensity values of the speckles captured by the CCD arrays (not shown) in camera 20. The intensity file is a large file consisting of a 256×256 array of intensity values. Only a small portion of this array need be selected, as in the exemplary embodiment where about a 5×5 array is selected. Hence, any 5 rows and 5 columns of each of the intensity file may be collected and grouped sequentially. That is, the $ij^{th}$ element of all the intensity files are collected. Next, the inventive Fast Fourier Transform (FFT) algorithm and processing (disclosed in greater detail below) is applied to this set of 25 new $ij^{th}$ intensity value files. The average or the normalized value of all the FFT values may then be obtained.

Figure 3:
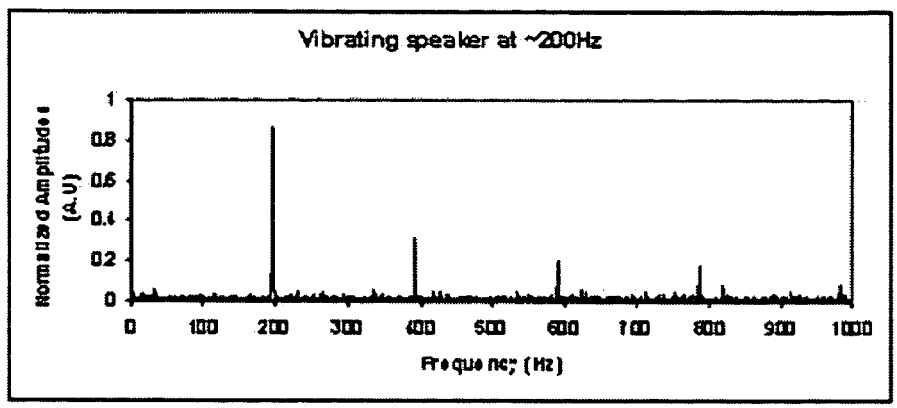
FIG. 3 is a graph view of an FFT plot of a speaker at a first frequency.
Figure 4:
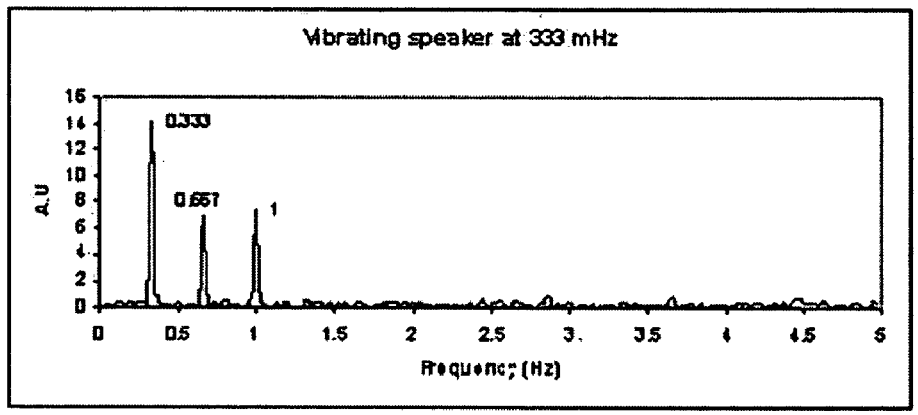
FIG. 4 is a graph view of an FFT plot of a speaker at a second frequency.
Figure 5:
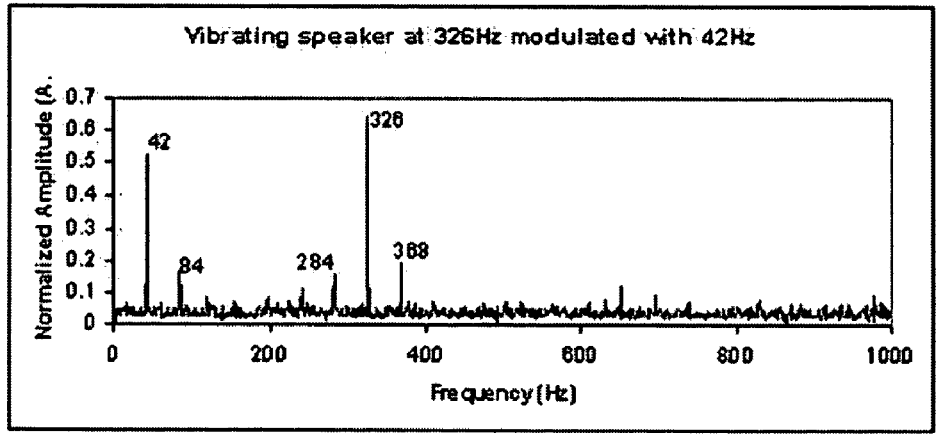
FIG. 5 is a graph view of an FFT plot of a speaker at a third frequency.

Specimen 16 may be observed by an audio speaker subjected to various frequencies from a sine wave oscillator. FIG. 3 shows the FFT obtained from a speaker vibrating at 200 Hz. Higher harmonics can also be observed. An external sinusoidal voltage of 200 Hz from a Sinewave generator is applied to the speaker. FIG. 4 shows a low frequency of 300 milli-Hz. System 10 is also sensitive to low frequencies. Modulated frequencies which involve more than a single frequency 326 Hz modulated at 42 Hz may also be carried out. The results of such multiple frequencies are plotted in FIG. 4. The frequency of vibration of a speaker at low frequency, high frequency and modulated frequency can be correctly determined by use of system 10 as shown in FIGS. 3 to 5.

Figure 6:
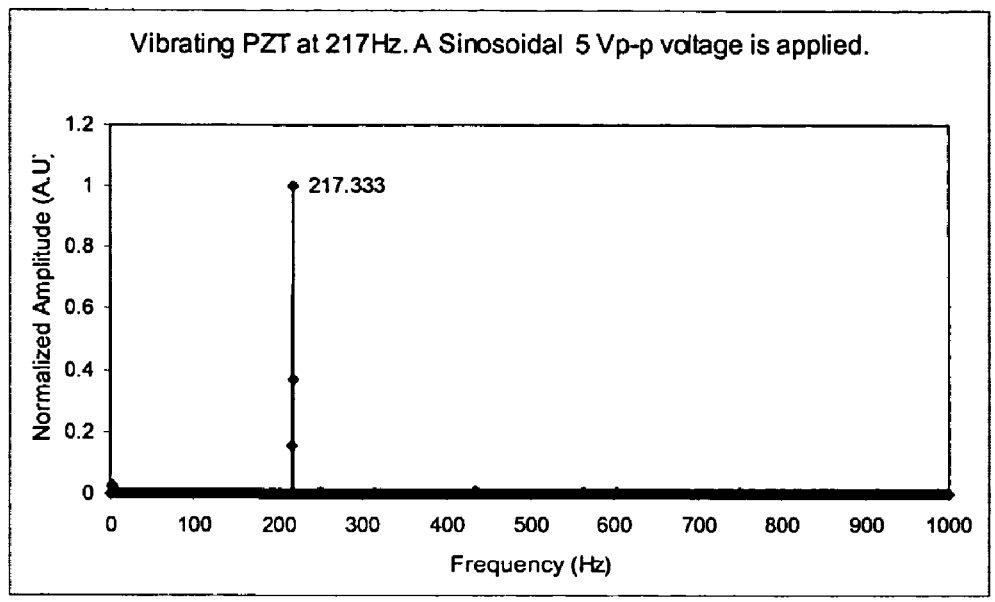
FIG. 6 is a graph view of an FFT plot of PZT at a first frequency.
Figure 7:
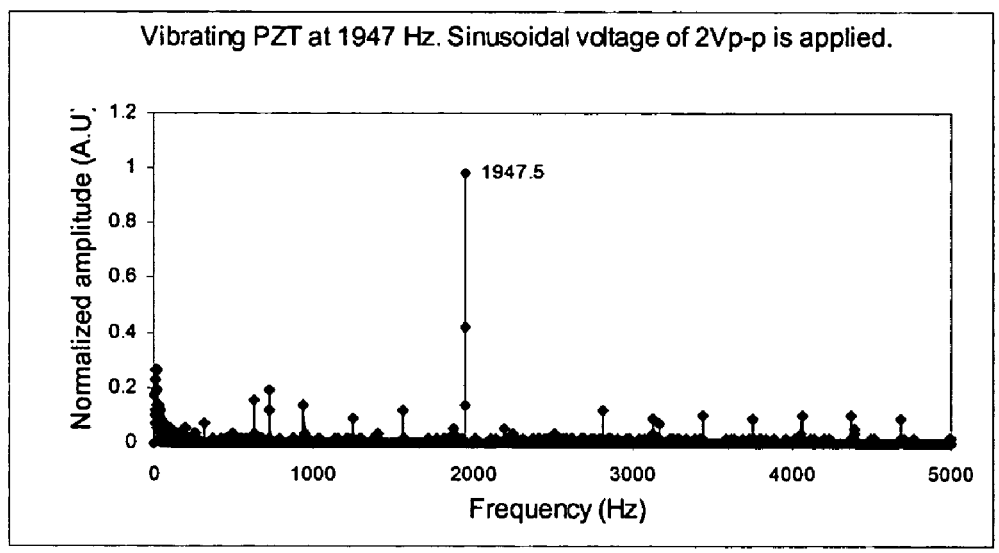
FIG. 7 is a graph view of an FFT plot of PZT at a second frequency.

Piezoelectricity is the phenomenon whereby electric dipoles are generated in certain anisotropic materials when subjected to mechanical stress. The same materials exhibit the converse effect in that they suffer a dimensional change under the influence of an electric field. Commercially available Piezoelectric transducers (PZT) have very small displacements of a several nanometers to few micrometers. A sinusoidal voltage applied to PZT will make it vibrate at the frequency of the applied voltage. In one exemplary embodiment, specimen 16 was observed with a PZT. The results indicate that frequencies of PZT with very small oscillation displacements of ~10–20 micrometers is detected by our apparatus as shown in FIGS. 6 to 7.

Figure 2:
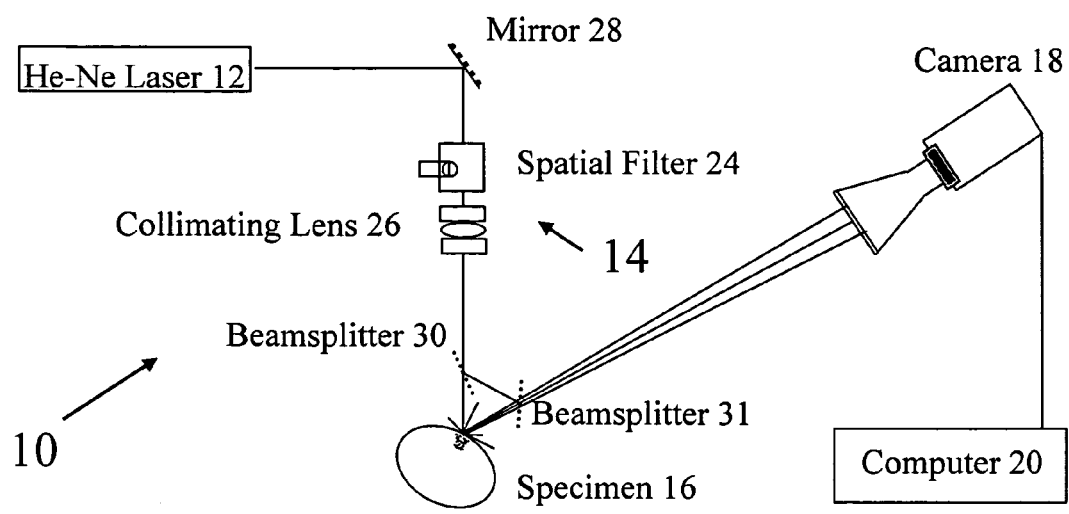
FIG. 2 is a schematic view of the system of the present invention with additional stability apparatus.

One embodiment of the invention includes use of two partial light reflectors such as beam-splitters or other kinds of optical elements to loop back partially reflected light. Beam-splitter 30 and 31 are placed in the path of the beam to form a ring configuration as shown in FIG. 2. The ring configuration is considered to be a Sagnac interferometer and in this invention enhances the stability of biospeckles and reduces the phase noise which is typical in laser induced speckles.

Biospecimen and living tissues are complex, seemingly random and full of uncertainties as with several natural phenomena. Many models and algorithms have been formulated for the prediction of matters involving such uncertain elements. One of them is Fractional Brownian motion. Brownian motion is referred to as the irregular and never-ending movement of microscopic particles in a fluid medium. Fractional Brownian motion is a generalization of Brownian motion in which the step size increments of particle displacements are not independent. In 1975, Mandelbrot coined the term Fractals. A fractal entity is characterized by the inherent, ubiquitous occurrence of irregularities which governs its contour and intricacy. In the real world, due to random events, complex patterns are formed that recur at various sizes and these images are fractals. The well understood fractal process is Brownian motion which can be constructed through a simple mathematical iteration. Every fractal process may be studied analytically. One of the methods of calculating fractional dimensions of fractals is by computing the FFT and then applying a linear regression technique on the log of the PSD obtained. Fractional dimension calculations (FDC) will give a unique value which is different for different naturally occurring phenomena such as ripening of a fruit or variation of glucose in blood. The FDC values are also distinctive during ripening process (unripe, ripe or overripe) and vary for different fruits.

A wavelet is a waveform with an average zero value and of typically small duration. In dealing with Fourier transforms analysis a signal is considered to be a combination of several sine waves. In Wavelet Transform Analysis (WTA) a signal is considered to be a combination of several shifted and scaled versions of an original wavelet also referred to as mother wavelet. WTA is capable of revealing aspects of data that other signal analysis techniques such as FFT, FDC are unable to. These include aspects like drift, singularities, discontinuities in higher derivatives, and self-similarity (as in Brownian motion). WTA may often compress or reduce noise factors that are inherent in the system. Thus in addition to FFT and FDC, WTA is a powerful post-processing tool that may enhance the accuracy of the present invention. FDC/WTA can be performed by Labview or Matlab. Matlab is a trademark of and produced by The MathWorks Inc, Natick, Mass.

The present invention is also applicable to the fields of Microelectromechanical Systems (MEMS) and Nanotechnology. MEMS technology incorporates the integration of tiny mechanical elements, sensors, actuators, and electronics on a common silicon substrate through micro-fabrication technology. It is the development of smart products, such as microsensors and microactuators which also have computational abilities. There are already a few commercially available MEMS devices such as 1) fluid pumps and valves, 2) Sensors to detect pressure, chemical, motion etc and 3) micro-optics in optical scanners, over-head projectors and mirror arrays. Nanotechnology relates to developing systems with atoms as the building blocks. It is believed that the first of the 'nanomachines' will be stronger fibers. Nanotechnology will be needed to create a new generation of computer components. Molecular computers may contain storage devices capable of storing trillions of bytes of information in a structure the size of a sugar cube. In the medical industry, nanorobots are medicines programmed to attack and reconstruct the molecular structure of cancer cells and viruses to make them harmless. Nanorobots could also be programmed to perform delicate surgeries—such nanosurgeons could work at a level a thousand times more precise than the sharpest scalpel. Many resources could be constructed by nanomachines. Micro and nano machines, engineered with MEMS and Nanotechnology, having moving parts or objects that move in a system tend to vibrate. The physical condition of such machines may be progressively ascertained by measuring the characteristic oscillation frequencies. Also, the thermal gradient on these micro & nano machine may alter the oscillation frequencies thereby making our invention detect overheating and prevent destruction of the machines.

System 10 may be used to determine the oscillation frequencies of a bio-specimen or a MEMS or nanotechnology system. In a bio-specimen there appears to be a lot of dynamic metabolic processes that take place in each of the cells. System 10 of the present invention investigates the characteristic oscillatory frequencies that may be due to the metabolic processes. For example, the exemplary embodiment was used to monitor the ripening of a banana because it ripens completely in a few days. The speaker is thus replaced with an unripe banana (not shown). The speckle pattern from the banana is collected by camera 18. The number of picture frames of the banana collected by camera 18 may be, for example, 2000 frames. Camera 18 is thus set to capture 2000 frames per second. The exposure time of each frame may be 75 micro-seconds. The total time to capture 2000 frames is thus around 2 seconds. Thus, system 10 and its underlying method of determining the FFT/FDC/WTA of bio-speckles can be used to measure or evaluate bioactivity phenomena such as ripening of fruits and monitoring human blood glucose level. In addition, system 10 may also be used to measure and/or evaluate the oscillatory frequencies of a MEMS or nanotechnology system. The process of measurement is also non-invasive and non-destructive.

The Fast Fourier Transform algorithm correlates time domain functions into frequency domain representations. The FFT in general is defined by the following equation:

$$X(f) = F\{x(t)\} = \int_{-\infty}^{\infty} x(t)e^{-i2\pi ft} dt,$$

where x(t) is a time varying signal and X(f) is the FFT signal. Power spectral density (PSD) described in [0020] is a method of scaling the amplitude of the signals and is more often used for random rather than deterministic input signals. PSD is defined in terms of amplitude squared per Hz, and is thus proportional to the power delivered by the signal in a one-Hz band. This is because a seemingly random signal has energy spread out over a frequency band rather than having energy concentrated at specific frequencies. We consider its amplitude within a fixed frequency band which is usually 1 Hz and not the RMS value at any specific frequency. The PSD which is closely related to the FFT is therefore used to calculate the harmonic power in a signal and is represented as the power spectrum $S_{xx}(f)$ of a time varying signal x(t) by the equation:

$S_{xx}(f)=X(f)X^*(f)=|X(f)|^2$, where $X(f)=F\{x(t)\}$ and $X^*(f)$ is the complex conjugate of $X(f)$. Hence the PSD format is identical to the real part of the FFT.

Thus, the system and method of the present invention may measure the 'oscillating frequencies' of vibrating surfaces. The frequencies may be as small as a few milli-hertz to as large as ~1000 Hz. The frequencies may also be much higher, based on the capture process as mentioned in the preceding paragraphs. A laser illuminates the specimen surface and light scattered from that surface at any angle is captured by a camera. A large number of pictures or frames are captured per second and each intensity value from the specific ij$^{th}$ row-column of the file is sorted and stored in the computer. A FFT (or FDC/WTA) is taken from all these values and normalized. The FFT peak gives the measure of the oscillation frequencies of the vibrating surface. A speaker or PZT may be subjected to several known frequencies and measured and confirmed by the system. The oscillatory frequencies of a biospecimen such as a fruit can also be measured and FFT/FDC/WTA calculations are expected to give values that correlate to the aging (ripening) of the fruit. Further, the oscillatory frequencies of a MEMS or nanotechnology system may be related to its temperature or other operating condition, allowing for observation of the operational characteristics of such systems. The present invention's system and method is non-invasive, non-destructive and is not subject to any specific orientation of the object.

The arrangement of the present invention allows for a low power single laser of any wavelength provided the camera can detect the particular wavelength of light. The arrangement of the present invention also allows for the object under study to be illuminated at any region, and the camera may be in any direction to capture the scattered light from the object. The expanded, collimated and spatially filter laser light allows for larger regions of illumination of the object. The completer portion of the illumination may be captured by the camera, but only a small portion (for example, $\frac{1}{100}^{th}$) is required for post processing (PSD & normalization and/or FDC/WTA & normalization). Also with the present invention, the higher the speed of the camera then images may be captured and the potential adverse effects of vibrations may be avoided without the use of an isolation table or the like. Also, the present invention provides that the object and the complete system need not be still for more than a second (similar to the expectation in conventional photography).

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A system for measuring speckle of a specimen, comprising:
   a source of coherent light being aimed at the specimen;
   a camera configured to obtain a plurality of images of the specimen, each of the plurality of images including an interference pattern formed by the interaction of the coherent light and the specimen absent an excitation of the specimen from an external source, the interference pattern including a speckle pattern; and
   a processor coupled to said camera, said processor including software configured to perform speckle analysis on the speckle pattern of each of the plurality of images, the speckle analysis including one of Fractional Dimensional Calculation analysis and Wavelet Transform analysis.

2. The system of claim 1 wherein said software is capable of converting images to intensity values.

3. The system of claim 2 wherein said software is capable of converting images stored in one of 8 bit bitmap, CIN, and JPEG formats.

4. The system of claim 2 wherein said software is capable of normalizing said intensity values.

5. The system of claim 1 wherein said camera is capable of obtaining at least one hundred images per second.

6. The system of claim 1 wherein said camera has a memory size capable of storing greater than 300 images.

7. The system of claim 1 wherein said software is capable of performing a Fourier transform analysis on said plurality of images.

8. The system of claim 1 wherein said software is capable of performing a Power Spectral Density analysis on said plurality of images.

9. The system of claim 1 wherein the speckle analysis includes the Fractal Dimension Calculation analysis.

10. The system of claim 1 wherein the speckle analysis includes the Wavelet Transform analysis.

11. The system of claim 1 wherein said source of coherent light is a laser.

12. The system of claim 11 further comprising an interferometer to enhance the stability of the speckle pattern of each of the plurality of images.

13. The system of claim 1 further comprising an optical device coupled to said source of coherent light and capable of expanding a beam of light emanating from said source of coherent light.

14. A method of measuring the vibration of a specimen, comprising the steps of:
projecting coherent light at a specimen;
obtaining a plurality of images of the specimen, each of the plurality of images including an interference pattern formed by the interaction of the coherent light and the specimen absent an excitation of the specimen from an external source, the interference pattern including a speckle pattern; and
performing speckle analysis on the plurality of images to determine a characteristic of the specimen, the speckle analysis including one of Fractional Dimensional Calculation analysis and Wavelet Transform analysis.

15. The method of claim 14 wherein said step of obtaining images includes obtaining at least one hundred images per second.

16. The method of claim 14 wherein said step of performing includes calculating a Fourier Transform analysis on the plurality of images.

17. The method of claim 14 wherein said step of performing includes calculating a Power Spectral Density analysis on the plurality of images.

18. The method of claim 14 wherein said step of performing includes calculating the Fractal Dimensional Calculation analysis on the plurality of images.

19. The method of claim 14 wherein said step of performing includes calculating the Wavelet Transform analysis on the plurality of images.

20. The method of claim 14 where said step of projecting includes projecting a laser at the specimen.

21. The method of claim 14 where said step of projecting includes forming a closed loop ring configuration to enhance the stability of the speckle pattern of each of the plurality of images.

22. A method of analyzing a specimen, comprising the steps of:
illuminating the specimen with a coherent light source;
obtaining a plurality of images of the specimen, each image including an interference pattern formed by the interaction of the coherent light and the specimen without the interaction of a separate reference beam of coherent light, the interference pattern being a speckle pattern; and
determining a time varying characteristic of the specimen based on an analysis of the speckle pattern formed by the interaction of the coherent light and the specimen through at least one of Fractional Dimensional Calculation analysis of the speckle pattern of each image and Wavelet Transform analysis of the speckle patter of each image.

23. The method of claim 22, wherein the specimen is a fruit and the time varying characteristic provides an indication of a ripeness of the fruit.

24. The method of claim 22, wherein the specimen is a human subject and the time varying characteristic provides an indication of a blood glucose level of the human subject.

25. The method of claim 22, wherein the specimen is a MEMS device and the time varying characteristic provides an indication of a physical condition of the MEMS device.

26. The method of claim 22, wherein the specimen is a nanotechnology system and the time varying characteristic provides an indication of a physical condition of the nanotechnology system.

27. The system of claim 1, wherein the specimen is a time-variant specimen.

28. The method of claim 14, wherein the specimen is a time-variant specimen.

29. The method of claim 22, wherein the specimen is a time-variant specimen.

30. The method of claim 22 further comprising the step of vibrating the specimen.

* * * * *